United States Patent
Yamada et al.

(10) Patent No.: US 7,252,960 B2
(45) Date of Patent: Aug. 7, 2007

(54) TEST KIT FOR INTRACELLULAR INTRODUCTION OF PROTEIN AND/OR PEPTIDE AND METHOD OF INTRACELLULAR INTRODUCTION

(75) Inventors: Hidenori Yamada, Okayama (JP); Junichiro Futami, Okayama (JP); Takashi Maeda, Okayama (JP); Midori Kitazoe, Okayama (JP); Hidetaka Nakanishi, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 386 days.

(21) Appl. No.: 10/671,881

(22) Filed: Sep. 29, 2003

(65) Prior Publication Data
US 2004/0115743 A1  Jun. 17, 2004

(30) Foreign Application Priority Data
Sep. 30, 2002  (JP)  ............................. 2002-287280

(51) Int. Cl.
*G01N 33/53* (2006.01)
*G01N 33/00* (2006.01)
(52) U.S. Cl. .................... 435/7.5; 536/23.1; 435/6; 435/7.1; 435/7.92; 435/320.1
(58) Field of Classification Search .................. 435/6, 435/7.1, 7.5, 7.92, 320.1, 455; 536/23.1
See application file for complete search history.

(56) References Cited

U.S. PATENT DOCUMENTS 6,312,727 B1 * 11/2001 Schacht et al. ............. 424/490
6,974,698 B1 * 12/2005 Miller et al. ................ 435/375
2005/0059031 A1 * 3/2005 Bruchez et al. ................ 435/6

FOREIGN PATENT DOCUMENTS

| EP | 1 316 318 A2 | 6/2003 |
| WO | WO 01/43778 A1 | 6/2001 |
| WO | WO 02/10201 A2 | 2/2002 |

OTHER PUBLICATIONS

Futami, J., et al, Preparation of Potent Cytotoxic Ribonucleases by Cationization: Enhanced Cellular Uptake and Decreased Interaction with Ribonuclease Inhibitor by Chemical Modification of Carboxyl Groups, Biochemistry 2001, 40: 7518-7524.
Schwarze, S.R., et al, In Vivo Protein Transduction: Delivery of a Biologically Active Protein into the Mouse, Science, vol. 285, No. 5433, Sep. 3, 1999: 1569-1572.
Futaki, S., et al, Arginine-rich Peptides, The Journal of Biological Chemistry, vol. 276, No. 8, Feb. 23, 2001: 5836-5840.

* cited by examiner

*Primary Examiner*—Herbert J Lilling
(74) *Attorney, Agent, or Firm*—Connolly, Bove, Lodge & Hutz, LLP (57) ABSTRACT

A test kit for intracellular introduction of a protein and/or peptide and a method of such intracellular introduction, make it possible for a protein and/or peptide to be introduced into cells efficiently and in an expedient manner while preventing the function of the introduction target protein and/or peptide from being reduced. The above test kit comprises a container containing a cationic group-containing polymer and a container containing a reagent for coupling or binding the cationic group-containing polymer to the protein and/or peptide, or comprises a container containing a cationized conjugate to be coupled to the protein and/or peptide. The above method comprises using a conjugate generated by coupling or binding a cationic group-containing polymer to a protein and/or peptide as a carrier for the introduction target protein and/or peptide.

2 Claims, 5 Drawing Sheets
(4 of 5 Drawing Sheet(s) Filed in Color)

By transmitted light  By fluorescence light

FIG. 3

By transmitted light  By fluorescence light

By
fluorescence
light

By
transmitted
light (i)        (ii)        (iii)

FIG. 8

TEST KIT FOR INTRACELLULAR INTRODUCTION OF PROTEIN AND/OR PEPTIDE AND METHOD OF INTRACELLULAR INTRODUCTION

TECHNICAL FIELD

The present invention relates to a test kit for intracellular introduction of a protein and/or peptide and to a method of such intracellular introduction. More particularly, it relates to a test kit for intracellular introduction which is to be used for allowing an arbitrary amount of a protein desired to function in cells to occur in cells for an arbitrary period of time and to an intracellular introduction method to be judiciously used in using such test kit for intracellular introduction.

BACKGROUND ART

The intracellular introduction technology of a protein is effective to know characteristics of the protein, and makes it possible for an arbitrary amount of the protein desired to function in cells to remain in cells for an arbitrary period of time. Currently, time signals of expression or modification of a protein engaged in proliferation, differentiation or development of various cells are being clarified. When applying these findings to engineering fields such as regeneration medicine or tissue engineering, by the intracellular introduction technology of a protein, it is expected to broaden various potentialities.

As for such the intracellular introduction technology of a protein, gene trasfer is used today. The gene trasfer is effective when the designated protein in cells is desired to function constantly. However, when the designated protein is desired to function transiently in cells, the method for introducing a protein itself into cells is in use.

Conventionally, as the intracellular introduction technology of a protein, Futami et al., "Biochemistry", Am Chem. Soc, 2001, Volume 40, Number 25, Pages 7518–7524 discloses a method using a highly cationic protein or a cationized protein by chemical modification.

Schwarze et al., "Science", Am Ass. For the Advancement of Science, 1999, Volume 285, Number 5433, Pages 1569–1572 discloses a method using a protein added a highly basic TAT peptide derived from HIV.

Futaki et al., "The Journal of Biological Chemistry", JBC, 2001, Volume 276, Number 8, Pages 5836–5840 discloses a method using a protein added a cationic peptide such as Poly-Arg.

As regards these techniques, it is presumable that the cationized protein, which is the target of introduction, is electrostatically adsorbed on the negatively charged cell surface and is thus taken up by cells with high efficiency. However, these techniques comprising protein cationization require some or other side chain modification of the introduction target protein molecule at a large number of sites, which leads to a decrease in the function of the protein. Further, there is room for contrivance for more easily making it possible for an arbitrary amount of the protein desired to function in cells to remain in cells for an arbitrary period of time so that the properties and the like of the protein may be studied efficiently for the application thereof in regeneration medicine or tissue engineering, for instance.

SUMMARY OF THE INVENTION

The present invention, which has been made in view of the above-described state of the art, has for its object to provide a test kit with which a protein and/or peptide can be introduced into cells in an efficient and expedient manner while preventing the function of the introduction target protein and/or peptide from being reduced, and a method of intracellular introduction which is judiciously utilized in using the above-mentioned test kit and the like.

The present inventors have already found that when a protein is cationized by modifying only a small number (one to at most several) of side chains of the protein with a cationic polymer, the decrease in function can be made slight (Japanese Patent Application No. 2002-156197). However, there is room for contrivance for minimizing the influences on the function and/or intracellular localization of the protein.

The present inventors made investigations concerning the technology of intracellular introduction of a protein and they paid attention to the fact that when an introduction target protein is partially cationized by coupling the protein with a cationic group-containing polymer, the cationized protein can be introduced into cells and, in this case, the function of the protein can be prevented from being reduced. Further, they also paid attention to the fact that such technology can be applied to the introduction of peptides into cells, and they found that a test kit comprising a container containing a cationic group-containing polymer and a container containing a reagent for coupling the cationic group-containing polymer to a protein and/or peptide is useful for introducing the protein and/or peptide into cells. They also found that a test kit in which a conjugate to be coupled to the protein and/or peptide is also useful for the same purpose. They came to realize that the above object can thus be successfully accomplished.

As regards the method of protein and/or peptide introduction into cells, they also found that the method which uses a conjugate generated by coupling of a cationic group-containing polymer to the protein and/or peptide as a carrier for the introduction target protein and/or peptide can produce the desired effects of the present invention, namely the efficient and expedient protein and/or peptide introduction into cells with the function of the introduction target protein and/or peptide being prevented from being reduced. Such findings have now led to completion of the present invention.

Modification of a protein and/or peptide molecule at a large number of amino acid side chain sites generally leads to a reduction in the function of the introduction target protein and/or peptide. When, however, a cationic group-containing polymer is used, a protein and/or peptide can be introduced into cells merely through partial modification of the protein and/or peptide with the polymer and, therefore, it becomes possible to prevent the function of the introduction target protein and/or peptide from being reduced. Thus, the present invention makes it possible to introduce a protein and/or peptide into cells in an efficient and expedient manner while assuring the sufficient working effect of the cationic group-containing polymer.

Therefore, the present invention is a test kit for introducing a protein and/or peptide into cells which comprises a container containing a cationic group-containing polymer and a container containing a reagent for coupling or binding the cationic group-containing polymer to the protein and/or peptide.

The present invention is also a test kit for introducing a protein and/or peptide into cells which comprises a container containing a cationized conjugate to be coupled to the protein and/or peptide.

The present invention is also a method of introducing a protein and/or peptide into cells which comprises using a conjugate generated by coupling or binding of a cationic group-containing polymer to a protein and/or peptide as a carrier for the introduction target protein and/or peptide.

DETAILED DISCLOSURE OF THE INVENTION

In the following, the present invention is described in detail.

The test kit of the present invention is used to form a cationized conjugate containing a protein and/or peptide, which is the target of introduction, for introducing the protein and/or peptide into cells. The cationized conjugate is taken up into cells. In accordance with the present invention, it becomes possible to introduce a protein and/or peptide into cells in an efficient and expedient manner while the function of the introduction target protein and/or peptide is prevented from being reduced.

The mode of formation of a cationized conjugate containing the introduction target protein and/or peptide in the above test kit includes (1) the mode in which the introduction target protein and/or peptide is coupled to the cationic group-containing polymer, and (2) the mode in which the introduction target protein and/or peptide is coupled to the cationized conjugate.

The cationic group-containing polymer to be used in the present invention may be any of the polymers having atoms capable of occurring as cations in an aqueous solution, for example, a polymer (copolymer) having one single species or a combination of two or more species of a polyalkylenepolyamine skeleton, a polyallylamine skeleton, a polyvinylamine skeleton, a poly(dialkylaminoalkyl (meth)acrylate) skeleton, a poly(meth) acrylic dialkylaminoalkylamide skeleton, a polyamidine skeleton, a polyvinylpyridine skeleton or polyvinylimidazole skeleton, and a copolymer thereof. Further, a salt of these polymers e.g. primary, secondary, tertiary, or quarternary ammonium salt are preferable. Among them, polyalkyleneimine which is a polymer having a polyalkylenepolyamine skeleton is preferred. Among the polyalkyleneimine, polyethyleneimine is more preferred. Additionally, those polymers, which are chemically altered or modified, may be used.

In the above-mentioned mode (1), a reagent for coupling or binding the cationic group-containing polymer to the protein and/or peptide to be used is preferable. When they are directly bound, suited for use as such reagents are, for example, dehydration/condensation agents such as 1-ethyl-3-(3-dimethylaminopropyl)-carbodiimide hydrochloride (EDC), N,N-dicyclohexylcarbodiimide(DCC); N-succinimidyl-3-(2-pyridyldithio)propionate(SPDP); 2-iminothiolane; N-(4-maleimidebutyryloxy)succinimide (GMBS) and the like. When there are bound via an intermediate like a spacer, it is preferable to use reagents such as a bifunctional crosslinking reagent and the like. Among these reagents, EDC is preferred.

In the above-mentioned mode (2), the cationized conjugate to be used is preferably one generated by coupling or binding of a cationic group-containing polymer to the protein and/or peptide. In this case, for example, (I) a conjugate generated by coupling or binding of the cationic group-containing polymer to avidin, which is one of the conjugate-forming proteins and/or peptides, by means of a reagent for coupling or binding the cationic group-containing polymer to proteins and/or peptides; (II) a conjugate generated by coupling or binding of the cationic group-containing polymer to protein A and/or protein G, which is one of the conjugate-forming proteins and/or peptides, by means of a reagent for coupling or binding the cationic group-containing polymer to proteins and/or peptides; or (III) a conjugate generated by coupling or binding of the cationic group-containing polymer to an antibody, which is one of the conjugate-forming proteins and/or peptides, by means of a reagent for the coupling or binding cationic group-containing polymer to proteins and/or peptides, for instance, is preferably used. In cases where the above-mentioned conjugate (I) is used, the protein and/or peptide is preferably biotinylated using a biotinylating agent and then coupled to avidin. When the above-mentioned conjugate (II) is used, an antibody is preferably used as the introduction target protein and/or peptide since antibodies readily bind to such conjugate. When the above-mentioned conjugate (III) is used, an antigen is preferably used as the introduction target protein and/or peptide since antigens readily bind to such conjugate. When a secondary antibody-containing conjugate, for instance, is used in such case, a primary antibody is preferably used as the introduction target protein and/or peptide.

The above-mentioned avidin, protein A and protein G include not only their naturally occurring forms but also forms genetically engineered for the purpose of improving their function.

In the case of the above-mentioned mode (1), the test kit of the present invention comprises a container (hereinafter sometimes referred to as "container 1") containing a cationic group-containing polymer and a container (hereinafter sometimes referred to as "container 2") containing a reagent for coupling or binding the cationic group-containing polymer to a protein and/or peptide.

In the case of the above-mentioned mode (2), the test kit of the present invention comprises a container (hereinafter sometimes referred to as "container 3") containing a cationized conjugate to be coupled to a protein and/or protein. In this case, the mode (2) may be one comprising a container containing a cationic group-containing polymer and a conjugate-forming protein and/or peptide and a container 2 containing a reagent for coupling or binding the cationic group-containing polymer to the protein and/or peptide; or one comprising a container containing a conjugate-forming protein and/or peptide, a container 1 containing a cationic group-containing polymer, and a containing container 2 containing a reagent for coupling or binding the cationic group-containing polymer to the protein and/or peptide In these cases, the method of using the test kit is not particularly restricted provided that there is formed a cationized conjugate containing the introduction target protein and/or peptide.

Preferred in the above mentioned mode (1) is, for example, a method comprising adding the introduction target protein and/or peptide to the container 1 and then adding the contents of container 1 to the container 2; or a method comprising adding the contents of container 1 to the container 2 and then adding the introduction target protein and/or peptide to the container 2.

In the above-mentioned mode (2), methods such as mentioned below are preferred.

(I) When a conjugate derived from a cationic group-containing polymer and avidin is used: a method comprising adding the introduction target protein and/or peptide in biotinylated form to a container 3 containing the conjugate derived from the cationic group-containing polymer and avidin; a method comprising preparing a container 3 using a container containing the cationic group-containing polymer and avidin and a container 2 containing a reagent for coupling or binding the cationic group-containing polymer to a protein and/or peptide, and adding the introduction target protein and/or peptide in biotinylated form to the container 3; and a method comprising preparing a container 3 using a container containing avidin, a container 1 containing the cationic group-containing polymer and a container 2 containing a reagent for coupling or binding the cationic group-containing polymer to a protein and/or peptide, and adding the introduction target protein and/or peptide in biotinylated form to the container 3.

(II) When a conjugate derived from a cationic group-containing polymer and protein A and/or protein G is used: the method comprising adding an antibody, which is the target of introduction, to a container 3 containing the conjugate derived from the cationic group-containing polymer and protein A and/or protein G; the method comprising preparing a container 3 using a container containing the cationic group-containing polymer and protein A and/or protein G and a container 2 containing a reagent for coupling or binding the cationic group-containing polymer to a protein and/or peptide, and adding an antibody, which is the introduction target, to the container 3; and the method comprising preparing a container 3 using a container containing protein A and/or protein G, a container 1 containing the cationic group-containing polymer and a container 2 containing a reagent for coupling or binding the cationic group-containing polymer to a protein and/or peptide, and adding an antibody, which is the target of introduction, to the container 3.

(III) When a conjugate derived from a cationic group-containing polymer and an antibody is used: the method comprising adding an antigen, which is the target of introduction, to a container 3 containing the conjugate derived from the cationic group-containing polymer and antibody; the method comprising preparing a container 3 using a container containing the cationic group-containing polymer and antibody for forming the conjugate and a container 2 containing a reagent for coupling or binding the cationic group-containing polymer to a protein and/or peptide, and adding an antigen, which is the target of introduction, to the container 3; and the method comprising preparing a container 3 using a container containing the antibody to form the conjugate, a container 1 containing the cationic group-containing polymer and container 2 containing a reagent for coupling or binding the cationic group-containing polymer to a protein and/or peptide, and adding an antigen, which is the target of introduction, to the container 3.

In these modes, the above conjugate-forming protein and/or peptide may be the same as or different from the introduction target protein and/or peptide. The protein and/or peptide may comprise one single species or a combination of two or more species.

In the mode (1) mentioned above, the proportion of the introduction target protein and/or peptide to the cationic group-containing polymer is preferably such that one to ten, more preferably one to three, molecules of the polymer are coupled to each molecule of the introduction target protein and/or peptide. The number of sites of binding of each polymer molecule to each protein and/or peptide molecule is preferably one. More preferably, the polymer is coupled to each protein and/or peptide molecule only at one site.

The cationic group-containing polymer to be contained in the container 1 is preferably in the form of an aqueous solution. More preferably, it is dissolved in water just prior to use and thus used in the form of an aqueous polymer solution. The concentration of the polymer in the aqueous polymer solution is preferably not less than 1% by mass but not more than 60% by mass. At a concentration lower than 1% by mass, the attempt to introduce a sufficient amount of a protein and/or peptide into cells may fail. At a concentration exceeding 60% by mass, the function and/or structure of a protein and/or peptide may not be fully retained any longer. A more preferred concentration is not lower than 5% by mass but not higher than 20% by mass.

The form of the above-mentioned reagent to be contained in a container 2 is not particularly restricted but may be in the form of a powder or in the form dissolved in a medium. The amount of the reagent is not particularly restricted but is selected so that it may be appropriate for the coupling of the polymer to the protein and/or peptide.

In the above-mentioned mode (2), the number of molecules of the above polymer to be coupled to each molecule of the protein and/or peptide for forming a cationized conjugate to be contained in the container 3, namely to each molecule of avidin in the above-mentioned mode (I), protein A and/or protein G in the mode (II) or an antibody in the mode (III), is not particularly restricted but preferably 1 to 10. The number of sites of binding of each polymer molecule to each protein and/or peptide molecule is preferably one. More preferably, the polymer is coupled to each protein and/or peptide molecule only at one site.

The mole ratio between the cationized conjugate in the container 3 and the introduction target protein and/or peptide is preferably 10/90 to 90/10, more preferably 20/80 to 80/20, in the above-mentioned mode (I). In the mode (II), the ratio is preferably 10/90 to 90/10, more preferably 30/70 to 70/30. In the above-mentioned mode (III), it is preferably 10/90 to 90/10, more preferably 30/70 to 70/30. In this way, the coupling, in the container 3, of the conjugate to the introduction target protein and/or peptide can be adequately carried out so that the effects of the present invention may be produced to a satisfactory extent.

The container each preferably has a capacity of 0.5 to 10 ml. These containers may be sterilized by autoclaving, ultraviolet irradiation, or gamma beam irradiation, for instance. The container inside may be coated for preventing mold growth and/or putrefaction of the substance within the container. Further, it is also preferred that the contents be charged into containers under an inert gas such as nitrogen or argon. After charging the above-mentioned substances into the respective containers, the containers are preferably stored in a tightly closed condition at low temperatures not exceeding 5° C.

Figure 1:
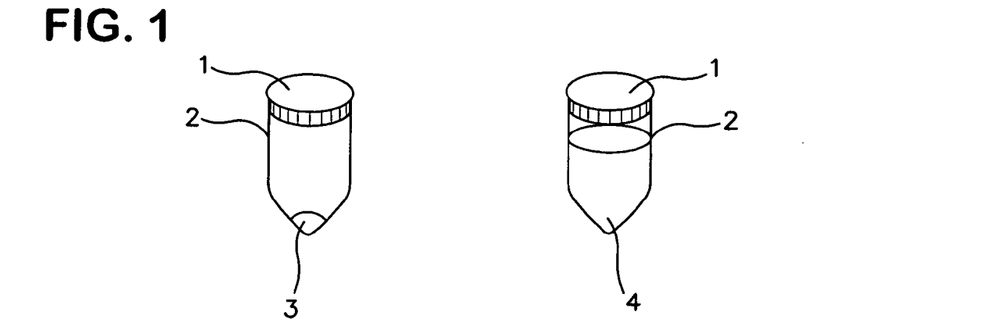
FIG. 1 is a schematic drawing illustrating the preferred embodiment of the test kit of the present invention.

One of the preferred embodiments of the test kit of the present invention comprises such a container or containers as shown in FIG. 1.

In the following, the test substances, reagents and so forth that can be used in the practice of the present invention are described in detail.

As the protein and/or peptide in the present invention, it can be used a compound produced by binding two or more amino acids with each other via a peptide bond. Usable as the protein and/or peptide is, for example, a peptide, an enzyme, an antibody, or a protein and/or peptide which has other functions (physiological activity such as pharmacological action) and is effective as a medicine or a drug. The molecular weight is preferably within a range of from 100 to 1,000,000. Incidentally, a protein and/or peptide in the present invention includes a conjugated protein and/or peptide formed by conjugation of a sugar chain, lipid and/or a phosphate group. Further, a structure thereof may either be a native state or a denatured state.

A cationic group-containing polymer in the present invention is preferred to be a polymer having a cation value of more than 2 and not more than 30,000. When the cation value is not more than 2, the functions of a protein and/or peptide binding to the cationic group-containing polymer will no longer be maintained effectively. When it exceeds 30,000, the working effects of the present invention may possibly be not fully produced. More preferably, it is not more than 20,000, still more preferably not more than 2,500, especially preferably not more than 250. Most preferably, it is not less than 4 and not more than 70.

The above-mentioned cation value is defined as a value obtained by dividing the product of the amine value of a polymer (mmol/g) and the number average molecular weight of the polymer by 1,000, and the amine value is an indicator of the total amine in a sample compound and it is represented as mmol number of amines that exist in 1 g of the sample compound. The amine value of the sample compound may be measured according to a known method for quantitative analysis of amino groups. As such quantitative analysis of amino groups, it can be used a method described in "Shin-jikkenn Kagaku Koza Vol. 13 Yuki-Kagaku-Kozo I" (Chemical Society of Japan, MARUZEN Co., Ltd., Nov. 20, 1978, p. 88–99) and Colloidal titration (R. Senju, "Colloidal titration method", 1st Ed., Nankodo Co., Ltd., Nov. 20, 1969). A suitable quantitative method should be chosen for accurate measurement of the amine value, in consideration of a form and solubility of the sample compound, and contaminants in the sample. The amine value of the above-mentioned polymer is preferably not less than 1 but not more than 30, more preferably not less than 5 but not more than 25.

A number average molecular weight of the above-mentioned cationic group-containing polymer is preferably not less than 100 but not more than 1,000,000 in consideration of efficiency for intracellular introduction and handling property. More preferably, it is not less than 100 but not more than 100,000, still more preferably not less than 100 but not more than 10,000, especially preferably not less than 200 but not more than 3,000. In addition, in the measurement method of the number average molecular weight of the polymer, for accurate measuring of the molecular weight, when the number average molecular is not more than 10,000, it is preferably to measure by the ebullioscopic method. When the number average molecular weight exceeds 10,000, it is preferably measured by gel permeation chromatography(GPC).

Suited for use as the above-mentioned cationic group-containing polymer are, for example, polyalkylenepolyamines such as polyalkyleneimines (e.g. polyethyleneimine, polypropyleneimine); polyallylamines such as polyallylamine and polydiallyldimethylammonium chloride; polyvinylamines such as Hofmann decomposition product of polyacrylamide, hydrolysate of polyvinylacetamide, a hydrolysate of polyvinylphthalimide and a hydrolysate of N-vinylformamide polymer; dialkylaminoalkyl (meth)acrylamide (co)polymers such as dimethylaminopropyl(meth)acrylamide (co)polymer; dialkylaminoalkyl(meth)acrylate (co)polymers such as polymethacryloyloxyethyl trimethylammonium chloride; polyamidine; polyvinylpyridine; polyvinylimidazole; a dicyandiamide condensate; epichlorohydrin-dialkylamine condensates such as an epichlorohydrin-dimethylamine condensate; dialkylamine-alkyldihalide condensates such as a dimethylamine-ethylenedichloride condensate; polyvinylimidazoline; polyvinylbenzyl trimethylammonium chloride; carboxy methyl cellulose quarternary ammonium (quarternary ammonium CMC); glycolchitosan; cationized starch and the like. Among these, polyalkyleneimine, which is a species of polyalkylenepolyamines, is preferable.

Following is the theoretical amine values of typical polymers among the above-mentioned cationic group-containing polymers.

TABLE 1

| | Amine value (mmol/g)* |
|---|---|
| polyethyleneimine | 23 |
| polyvinylamine | 23 |
| polyallylamine | 17 |
| polydiallyldimethylammonium chloride | 6.2 |
| polymethacryloyloxyethyl trimethylammonium chloride | 4.8 |
| polymethacryloylaminopropyl trimethylammonium chloride | 4.5 |
| polyamidine | 6.0 |
| polyvinylbenzyl trimethylammonium chloride | 6.3 |
| polyvinylpyridine | 10 |
| polyvinylimidazole | 11 |
| epichlorohydrin-dimethylamine condensate | 7.2 |
| dimethylamine-ethylenedichloride condensate | 9.3 |

*theoretically maximum value

In the above table 1, the theoretical amine values are calculated by multiplying a reciprocal of molecular weight of a component monomer of the polymer by 1,000. Generally, the amine value experimentally determined by the above-mentioned method is almost identical with the theoretical value within a range of measurement errors. The cation value of the polymer may be calculated on the basis of the amine value determined by the above-mentioned method. The amine value may be optionally varied by changing a synthesizing method of the polymer, copolymerizing with other components, or chemical modification of the polymer.

As the polyalkyleneimine, for example, a compound represented by the following general formula (1) is preferably used:

(1)

In the above general formula (1), $R^1$, $R^2$, and $R^3$ are the same or different and each represents an alkylene group. X and Y are the same or different and each represents an integer of 0 or more. Further, the compound may be either the compound having a linear chain or a branched structure.

As the above polyalkyleneimine, the compound is preferably that $R^1$, $R^2$, and $R^3$ represent an alkylene group containing 2 to 4 carbon atoms. More preferably, it is polyethyleneimine which is the compound that $R^1$, $R^2$, and $R^3$ represent an alkylene group containing 2 carbon atoms.

Suited for use as the cationic group-containing polymer in the present invention is polyethyleneimine as mentioned above. As such polyethyleneimine, for example, a compound represented by the following general formula (2) is preferably used:

(2)

In the above general formula (2), x and y are each an integer of 1 or more.

The above-mentioned polyethyleneimine(PEI) is a water-soluble polymer having a large positive charging density and used as a food additive such as a precipitant for fish sausage. Although either a PEI having a linear chain or a PEI having a branched structure with many branch chains may be used, a PEI having a branched structure represented by the following general formula (3) is preferable due to its high positive charging density.

(3)

In the above-mentioned mode (1), the bond between the cationic group-containing polymer and the introduction target protein and/or peptide is preferably a covalent one. By utilizing various synthetic techniques, it is possible to realize the bonding/coupling in various manners of bonding. For example, when using polyethyleneimine as the cationic group-containing polymer, and dehydration/condensation agents such as EDC, DCC as the reagent for coupling or binding the cationic group-containing polymer to the protein and/or peptide, an amide bond can be formed between an amino group of the PEI and an asparatic acid residue, a glutamic acid residue, or a carboxyl group of C-terminal in the protein and/or peptide molecule. An example case wherein EDC is used is schematically shown below.

protein and/or peptide

When using SPDP and the like as the above reagent, a covalent bond including disulfide bond can be formed between an amino group of the PEI and a thiol group of a cysteine residue in the protein and/or peptide molecule. An example case wherein SPDP is used is schematically shown below.

The above disulfide bond is reversible, and it dissociates under reducing condition in the cytoplasm. Therefore, when the conjugate formed by disulfide bond is introduced into cells, the PEI is separated from the protein and/or peptide, and thus the protein and/or peptide is expected to exhibit its function more advantageously in cells.

When using 2-iminothiolane and the like as the above reagent, an amino group of the PEI can be bind to a lysine residue or an amino group of N-terminal in the protein and/or peptide molecule. And, when using GMBS and the like, a covalent bond including thioether bond can be formed between an amino group of the PEI and a thiol group of a cysteine residue in the protein and/or peptide molecule.

When using the other reagents, for example, ether bond, ester bond, imide bond, carbon-carbon bond, amidine bond and the like can be formed. In these binding methods, various binding methods can be employed with reference to the literature (e.g. Tokyo Kagaku Dozin, "Tanpakushitu IV Kouzoukino-sokan (Protein IV Correlation between structure and its function)", The Japanese Biochemical Society, 1st edition, Mar. 20, 1991).

When, in the above-mentioned mode (2), a cationized conjugate is used as a carrier for the introduction target protein and/or peptide, the conjugate can be reversibly coupled to the introduction target protein and/or peptide. This reversible coupling may be a direct reversible coupling of the conjugate to the introduction target protein and/or peptide or a coupling via a spacer capable of reversibly binding the conjugate to the introduction target protein and/or peptide, for instance. The "coupling or bonding" so referred to herein includes, within the meaning thereof, coupling/bonding and/or association.

Preferably, the introduction target protein and/or peptide is coupled to a part of the cationized conjugate-forming protein and/or peptide. This coupling preferably comprises a reversible noncovalent bond. The introduction target protein and/or peptide and the cationized conjugate can be considered to be in the same relationship as that between a protein and a ligand for the protein, for instance. The ligand for protein is a compound having affinity for a specific protein and binding to that protein in a noncovalent manner, for example a substrate or coenzyme against an enzyme, an antigen against an antibody, or biotin against avidin or streptavidin.

As the manner of coupling/bonding between the introduction target protein and/or peptide and the cationized conjugate, there may be mentioned, for example, the bonding between avidin and biotin; the bonding between staphylococcus-derived protein A and/or protein G and any of various mammalian and other antibody subclass: IgG Fc fragments; and the bonding between a secondary antibody recognizing the Fc site of an antibody and a primary antibody. The protein and/or peptide to be introduced into cells can be coupled to the protein and/or peptide in the conjugate by utilizing one of such manners of bonding. Thus, by using, as a component of the conjugate, a protein and/or peptide having affinity for the introduction target protein and/or peptide, it is possible to allow the protein and/or peptide in the conjugate to bind to the introduction target protein and/or peptide merely by mixing the conjugate and the introduction target protein and/or peptide together. The bond between the introduction target protein and/or peptide and the conjugate may be a bond cleavable in cells. Such intracellularly cleavable bond includes the form cleavable at the site of a spacer inserted between the introduction target protein and/or peptide and the conjugate.

Figure 2:
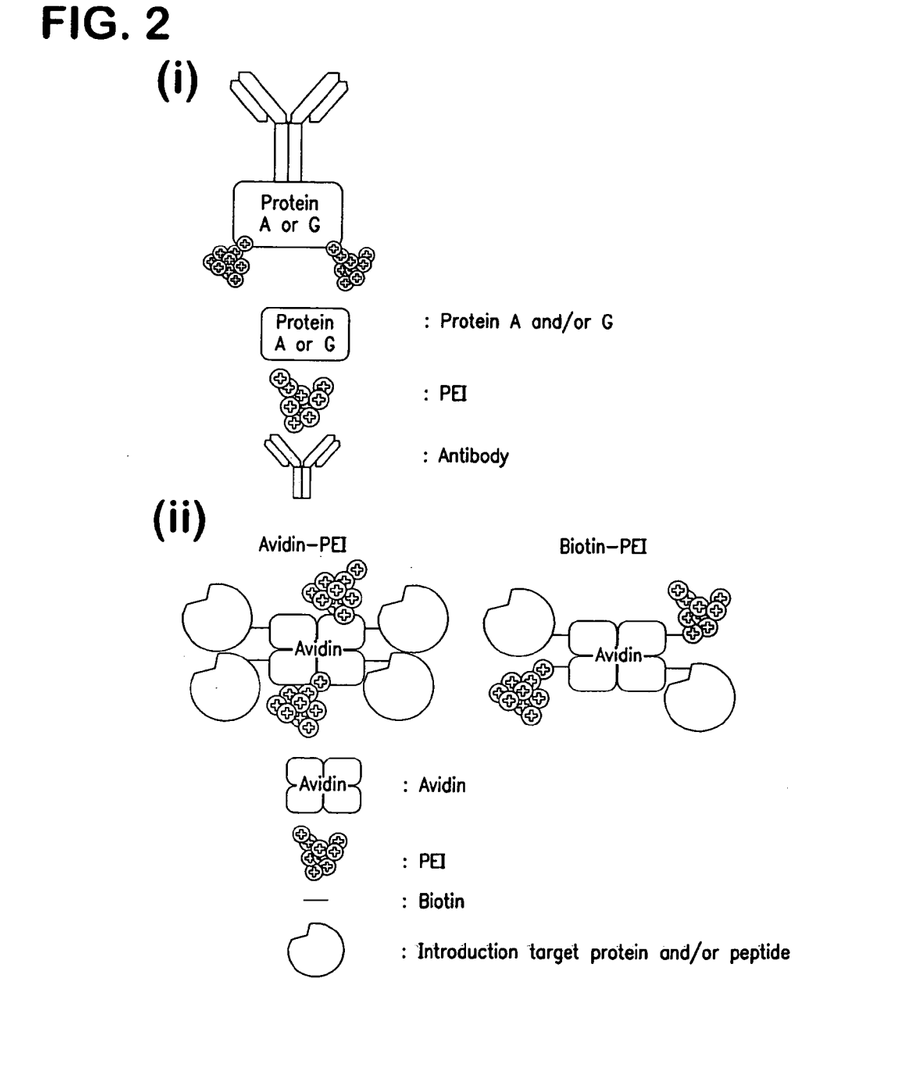
FIG. 2 is a schematic drawing illustrating the relations among the conjugate-forming protein and/or peptide, cationic group-containing polymer and introduction target protein and/or peptide.

FIG. 2 is a schematic drawing illustrating the relations among the conjugate-forming protein and/or peptide, cationic group-containing polymer and introduction target protein and/or peptide in the above-mentioned mode (2). In FIG. 2 (i), there is shown an example in which protein A and/or protein G is used as the conjugate-forming protein and/or peptide, polyethyleneimine (PEI) as the cationic group-containing polymer, and an antibody as the introduction target protein and/or peptide and, in (i), it is shown that PEI and protein A and/or protein G form a conjugate, and this conjugate and the antibody bind to each other. In (ii), there is shown an example in which avidin is used as the conjugate-forming protein and/or peptide, PEI as the cationic group-containing polymer, and biotin as a spacer between the conjugate-forming protein and/or peptide and the introduction target protein and/or peptide and, in (ii), it is shown that PEI and avidin form a conjugate and this conjugate and the introduction target protein and/or peptide in biotinylated form bind to each other.

The conjugate to be produced or used in the present invention, if necessary, may be labeled. The labeling method is not particularly restricted, but preferably is a method using such as fluorescent labeling, autoradiography, high electron-dense material, and insoluble pigment enzyme. Especially preferred is a method comprising labeling the conjugate by covalently binding the conjugate with the fluorescent labeling compound.

Fluorescent substances to be used for fluorescent labeling are not particularly restricted and, for example, the compounds having a fluorescent group such as pyrene, ananthraniloyl group, a dansyl group, fluorescein, rhodamine, or nitrobenzoxadiazol. The compounds having the above fluorescent groups are disclosed in the literatures (refer to e.g., Hiratsuka Toshiaki, "Tanpakushitu, Kakusan, Koso", 1997, Vol. 42, No. 7), and these compounds can be introduced into protein molecules or peptides by conventional methods.

The method of the present invention for intracellular introduction of a protein and/or peptide is a method of introducing a protein and/or peptide into cells, and the intracellular introduction method mentioned above comprises using a conjugate generated by coupling or binding of a cationic group-containing polymer to a protein and/or peptide as a carrier for the introduction target protein and/or peptide. In accordance with such method of intracellular introduction, the above-mentioned conjugate and the introduction target protein and/or peptide are coupled to each other and the coupling product is brought into contact with cells, whereby the product can be effectively introduced into cells while the structure and function of the protein and/or peptide is maintained.

The above method of intracellular introduction is judiciously applied in using the test kit of the present invention. However, the application of the method is not particularly limited to the use of such test kit.

In the above method of intracellular introduction, a cationic group-containing polymer is preferred to be a polymer having a cation value of more than 2 and not more than 30,000.

Referring to the above method of intracellular introduction, the mode of conjugate formation by cationic group-containing polymer-to-protein and/or peptide coupling and the mode of binding of the conjugate to the introduction target protein and/or peptide are preferably the same as the mode (1) and mode (2) respectively described hereinabove referring to the test kit of the present invention. For example, in the above intracellular introduction method, the conjugate-forming protein and/or peptide preferably comprises at least one protein and/or peptide selected from the group consisting of avidins, protein A and/or protein G, and antibodies. When avidins are used as the conjugate-forming protein and/or peptide, the introduction target protein and/or peptide is preferably used in the form biotinylated by means of a biotinylating agent and this is preferably caused to bind to avidin. When protein A and/or protein G is used as the conjugate-forming protein and/or peptide, an antibody is preferably used as the introduction target protein and/or peptide, since antibodies readily bind to such conjugate. And, when an antibody is used as the conjugate-forming protein and/or peptide, an antigen is preferably used as the introduction target protein and/or peptide, since antigens readily bind to such conjugate. When a secondary antibody-containing conjugate, for instance, is used in such the case, a primary antibody is preferably used as the introduction target protein and/or peptide.

In carrying out the method of the present invention for introducing the introduction target protein and/or peptide into cells using a cationized conjugate containing the introduction target protein and/or peptide, for instance, the following method is judiciously used.

The conjugate produced in accordance with the present invention or a solution containing the same is added to a medium containing cells into which the protein and/or peptide is to be introduced. Thereafter, the cells are cultivated under appropriate conditions including culture temperature, culture period and so on. Therefore, the conjugates are incorporated into cells, and the amount of the conjugates incorporated into cells is increased with the passage of time. In such method, the amount of protein and/or peptide to be introduced into the cells can easily be controlled by changing the absolute amount, concentration, period for adding of the conjugates, and the like.

In the above introduction method, it is assumed that the conjugates are incorporated into cells by a mechanism attributable to electrostatic interaction between the positively charged conjugates and a negatively charged cell surface. Thus, for incorporation of the conjugates into cells in the medium, it is preferable to carry out the above process in the absence of anionic polymers such as heparin and nucleic acid. Further, the solution containing the above conjugates may be inoculated directly into a living body by a method e.g. oral administration, intravenous administration, injection to an affected part, and dermal application, thus allowing conjugates to be incorporated into cells of the living body.

The intracellular introduction technology of a protein and/or peptide in the present invention may be employed for applications of in vivo function analysis of proteins and/or peptides, and further for medical products, medicines, reagents, support for drug development, and regenerative medicine. Such embodiment is one of the preferred forms of embodiment of the present invention. Preferred embodiments include, for example, a conjugate which is formed by binding a protein and/or peptide as a pharmaceutical agent (e.g., enzymes, antibodies, and hormones) having physiological activity (e.g. pharmacological action) with the cationic group-containing polymer(e.g. polyethyleneimine) can be used as a medicine. Such medicines are very useful since the cationic group-containing polymer works as a carrier to efficiently deliver the pharmaceutical protein and/or peptide into cells. The method also has a capability of being applied to a therapeutic method which comprises introducing a protein and/or peptide into cells extracorporeally (ex vivo) and returning the cells again to the living body.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(i) shows an example in which protein A and/or protein G is used as the conjugate-forming protein and/or peptide, polyethyleneimine (PEI) as the cationic group-containing polymer, and an antibody as the introduction target protein and/or peptide.

(ii) shows an example in which avidin is used as the conjugate-forming protein and/or peptide, PEI as the cationic group-containing polymer, and biotin as a spacer between the conjugate-forming protein and/or peptide and the introduction target protein and/or peptide.

DESCRIPTION OF REFERENCE NUMERALS

1 Cover
2 Container
3 Dehydration/condensation agent
4 Aqueous solution of PEI

BEST MODE FOR CARRYING OUT THE INVENTION

The following examples illustrate the present invention in further detail without defining the scope of the invention. Unless otherwise indicated, "percentage (%)" means "mass %".

EXAMPLE 1

Preparation of Test Kit A for Intracellular Introduction

A 0.8 ml portion of an aqueous solution (adjusted to pH 5 with hydrochloric acid) containing 30 mg/ml of polyethyleneimine with a number average molecular weight of 600

(product of Wako Pure Chemical Industries, catalog number 161-17831; hereinafter referred to as "PEI 600") was filled in a container 1 (1.5 ml plastic-made tube for dialysis and storage) and sealed under nitrogen gas. Separately, 2 mg of EDC (1-ethyl-3-(3-dimethylaminopropyl)carbodiimide hydrochloride, product of PIERCE) was filled in a container 2 (1.5 ml plastic-made tube for dialysis and storage) and sealed.

Introduction of eGFP-PEI Conjugate into Cells

As a protein, eGFP (Enhanced Green Fluorescent Protein, product of CLONTECH) was used. The eGFP contains His tag at the amino terminal, and it was expressed in *Escherichia coli* as a recombinant protein and purified.

2 mg of eGFP was dissolved in the container 1 of the test kit A. Using a pipette, the whole quantity of the solution in the container 1 was poured into the container 2, and it was left at room temperature for 3 hours. An eGFP-PEI conjugate was obtained by sufficiently dialyzing the solution in the container 2 against ultrapure water.

Figure 3:
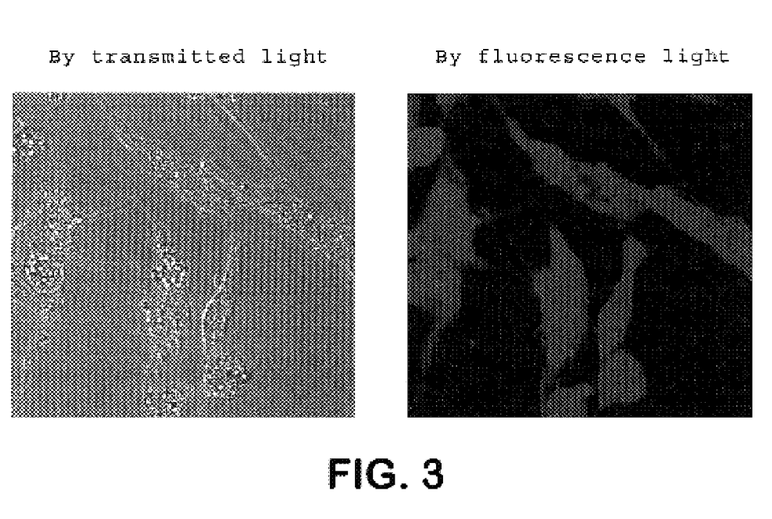
FIG. 3 shows observation views by fluorescent light and transmitted light, which show the incorporation of eGFP-PEI conjugates into Balb/c3T3 A31K cells.

Balb/c3T3 A31K cells were cultivated in DMEM+10% FBS, and 100 nM (3 µg/ml) of eGFP-PEI conjugates were added to the culture supernatant. After 8 hours, the cell was observed by a confocal microscope. The result is shown in FIG. 3. As can be seen from FIG. 3, it was confirmed that the eGFP-PEI conjugates were effectively incorporated into cells. Incidentally, the fluorescence observation was conducted on live cells, and fixation etc. was not carried out.

EXAMPLE 2

Preparation of Test Kit B for Intracellular Introduction 5 mg of Recombinant protein G (product of Sigma, catalog number P5170) was dissolved in 60 mg/ml of a PEI 600 solution (adjusted to pH 5 with hydrochloric acid) so as to have a concentration of 0.5 mg/ml. The protein G solution was added with 5 mg of EDC (product of PIERCE), and the mixture was allowed to stand overnight at 4° C. The unreacted portion of PEI was removed by dialysis against ultrapure water to give a protein G-PEI conjugate. The obtained protein G-PEI concentration was adjusted to 1 µM, and 1.0 ml of the solution was filled in a container (1.5 ml plastic-made tube for dialysis and storage) and sealed.

Introduction of Protein G-PEI Conjugate into Cells

In the conventional way, a solution adjusted to 4 µM concentration of the FITC labeled IgG (rabbit origin) was prepared.

The following experiments were conducted using the test kit B prepared as mentioned above.

Figure 4:
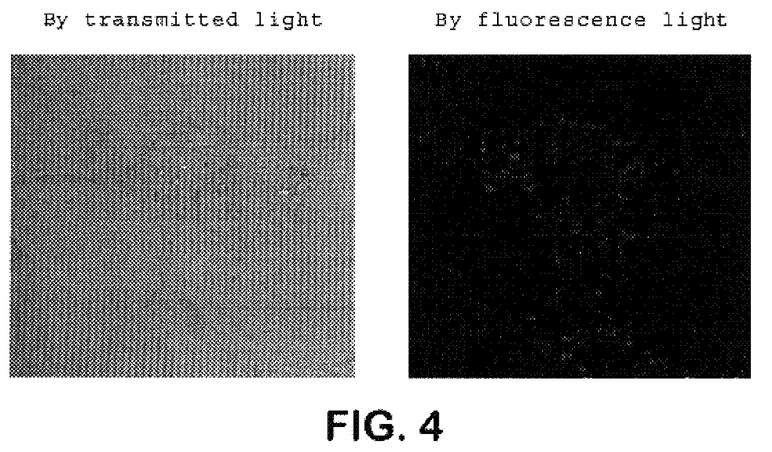
FIG. 4 shows observation views by fluorescent light and transmitted light, which show the incorporation of Protein G-PEI conjugates into Balb/c3T3 A31K cells.

100 µl of the Protein G-PEI solution and 100 µl of FITC labeled IgG solution were mixed, and the mixture was left on ice for 30 minutes. Balb/c3T3 A31K cells were cultivated on DMEM+10% FBS. To the culture supernatant, the Protein G-PEI conjugates were added so as to have a concentration of 25 nM. After 3 hours, the cell was observed by a confocal microscope. The result is shown in FIG. 4. As can be seen from FIG. 4, it was confirmed that the Protein G-PEI conjugates were effectively incorporated into cells. Incidentally, the fluorescence observation was conducted on live cells, and fixation etc. was not carried out.

EXAMPLE 3

Preparation of Test Kit C for Intracellular Introduction 1 mg of avidin was dissolved in 1 ml of a PEI 600 solution (adjusted to pH 5 with hydrochloric acid). 5 mg of EDC was added, and the mixture was stirred by means of a vortex mixer for 30 seconds and then incubated at room temperature for 2 hours. The reaction solution was dialyzed against water and the dialyzate was lyophilized. Thereto was added 1 ml of a 0.5 M solution of hydroxylamine, and the mixture was incubated at room temperature for 5 hours. After completion of the reaction, the reaction mixture solution was dialyzed against water to give avidin-PEI.

The concentration of the thus-obtained avidin-PEI was adjusted to 0.1 µM, and 1.0 ml of the solution was filled in a container 1 (1.5 ml plastic-made tube for dialysis and storage) and sealed. A 100 µl portion of a solution prepared by dissolving biotin-AC5-OSU (product of Dojin Kagaku) in DMF (N,N-dimethylformamide) so as to have a concentration of 2 mg/ml was filled in a container 2 (1.0 ml plastic-made tube for dialysis and storage) and sealed.

Introduction of biotin-eGFP+avidin-PEI Conjugate into Cells

The following experiments were conducted using the test kit C prepared as mentioned above.

1 ml of a solution dissolving eGFP used in Example 1 in PBS (Phosphate buffer saline) was prepared so as to have a concentration of 2.5 mg/ml. To this solution, the solution in the container 2 was added. The Biotin-eGFP solution was obtained by dialyzing the mixture against water.

Figure 5:
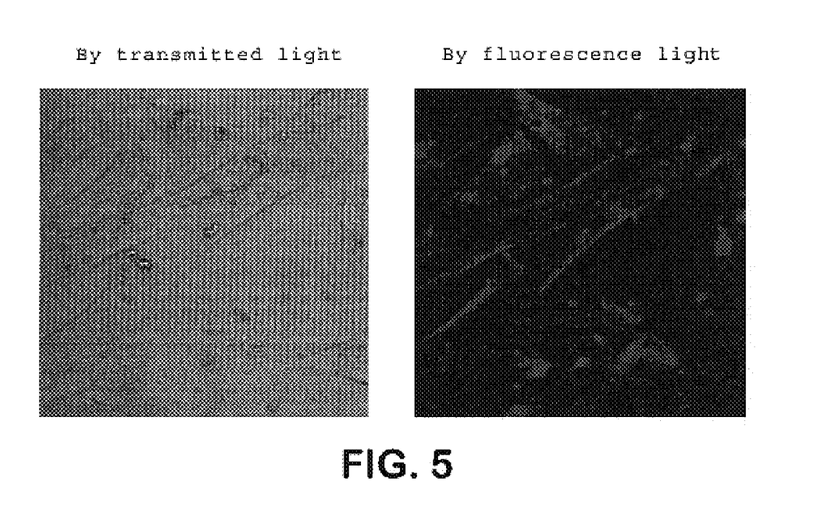
FIG. 5 shows observation views by fluorescent light and transmitted light, which show the incorporation of Biotin-eGFP +Avidin-PEI conjugates into Balb/c3T3 A31K cells.

The avidin-PEI in the container 1 and the biotin-eGFP solution were mixed so as to be the avidin-PEI/the biotin-eGFP solution mole ratio of 1/2, and left the mixture for 30 minutes on ice. Balb/c3T3 A31K cells were cultivated on DMEM+10% FBS. To the culture supernatant, the above mixture was added so as to have a concentration of 100 nM of the avidin-PEI and 200 nM of the biotin-eGFP, respectively. After 3 hours, the cell was observed by a confocal microscope. The result is shown in FIG. 5. As can be seen from FIG. 5, it was confirmed that the Biotin-eGFP+Avidin-PEI conjugates were effectively incorporated into cells. Incidentally, the fluorescence observation was conducted on live cells, and fixation etc. was not carried out.

EXAMPLE 4

Biotin and/or avidin was used as the conjugate-forming protein and/or peptide, PEI (product of Wako Pure Chemical Industries, catalog number 161-17831; molecular weight 600, cation value 12) as the cationic group-containing polymer, and eGFP (product of CLONTECH) allowing protein introduction into cells to be easily observed by fluorescence light as the introduction target protein and/or peptide.

Preparation of Biotinylated eGFP eGFP was dissolved in PBS with a concentration of 2.5 mg/ml. To the eGFP solution was added with 37.9 µl of a 2 mg/ml solution of biotin-AC$_5$-OSu (product of Dojin Kagaku) in DMF (N,N-dimethylformamide), and the mixture was stirred by means of a vortex mixer for 30 seconds and then incubated at room temperature for 3 hours. The reaction solution was purified by gel filtration chromatography (PD10) to give biotinylated eGFP.

Preparation of biotin-PEI Conjugate

Biotinylated PEI was prepared by the following procedure.

76 µl of a biotin-AC$_5$-Osu solution (dissolved in DMF) with a concentration of 1 mg/ml was added to 418 µl of a 30 mg/ml aqueous solution of PEI (adjusted to pH8 with hydrochloric acid). The reaction was carried out by 7 hours of incubation at room temperature and, after completion of the reaction, the reaction mixture was stored at 4° C. until the time of use. The concentration of biotinylated PEI was adjusted to the final biotin concentration, 33.8 mM.

Preparation of avidin-PEI Conjugate 1 mg of avidin was dissolved in 1 ml of an aqueous solution of PEI with a concentration of 60 mg/ml (adjusted to pH 5 with hydrochloric acid). 30 mg of EDC was added, and the mixture was stirred by means of a vortex mixer for 30 seconds and then incubated at room temperature for 16 hours. The reaction mixture was dialyzed against water and then lyophilized. The lyophilization product was dissolved in 1 ml of a 0.5 M solution of hydroxylamine, the solution was incubated at room temperature for 5 hours and, after completion of the reaction, the reaction mixture was dialyzed against water to give avidin-PEI.

Introduction of Biotinylated eGFP into Cells

The cell strain 3T3-SV-40 was cultured in DMEM+10% FBS. With portions of the culture supernatant were respectively admixed three samples, namely (i) biotin-eGFP (200 nM) (6 ug/ml), (ii) biotin-eGFP (200 nM)+avidin (100 nM)+biotin-PEI (200 nM) conjugate, and (iii) biotin-eGFP (200 nM)+avidin-PEI (50 nM) conjugate and, for each sample, the incorporation of eGFP after 24 hours was observed in fluorescent light and transmitted light. The results are shown in FIG. 6.

Figure 6:
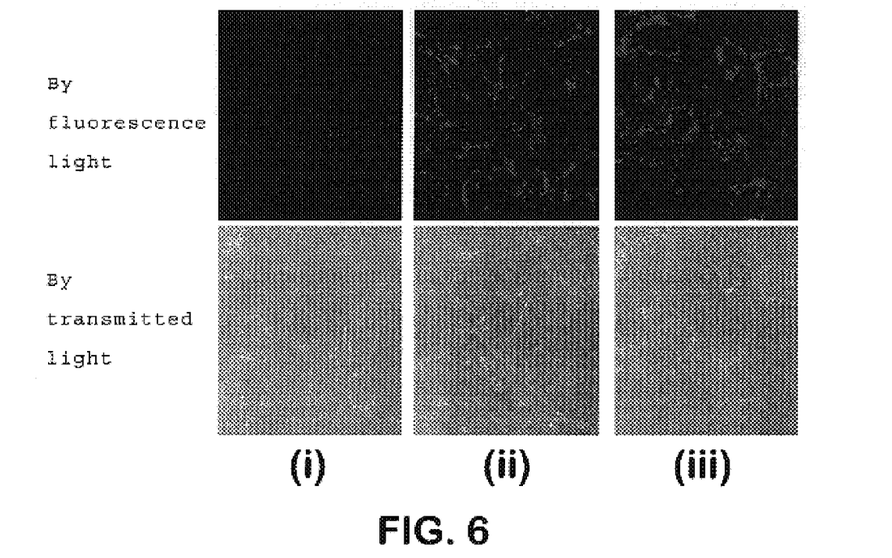
FIG. 6 shows observation views by fluorescent light and transmitted light, which show the incorporation of biotinylated eGFP into cells. (i) is an observation view using Biotin-eGFP, (ii) is using Biotin-eGFP+Avidin+Biotin-PEI conjugates, (iii) is using Biotin-eGFP+Avidin-PEI conjugates.

As is evident from the observation results shown in FIG. 6, with the sample (i), namely biotin-eGFP alone, almost no eGFP was incorporated into cells, whereas, with either of the sample (ii), namely biotin-eGFP (200 nM)+avidin (100 nM)+biotin-PEI (200 nM) conjugate, and the sample (iii), namely biotin-eGFP (200 nM)+avidin-PEI (50 nM) conjugate, eGFP was efficiently incorporated into cells.

This is presumably due to the formation of such cationized forms of avidin (conjugates) as shown in FIG. 2 with the samples (ii) and (iii), which served as carriers for biotinylated eGFP (introduction target protein and/or peptide), with the result that biotinylated eGFP was efficiently introduced into cells. Fluorescent observations were carried out with live cells, without fixation or like treatment.

EXAMPLE 5

Protein G was used as the conjugate-forming protein and/or peptide, PEI (product of Wako Pure Chemical Industries, catalog number 161-17831; molecular weight 600, cation value 12) as the cationic group-containing polymer, and a rhodamine-labeled rabbit IgG antibody against mouse IgG (hereinafter referred to as "rhodamine-rIgG") as the introduction target protein and/or peptide.

Preparation of Protein G-PEI Conjugate

A conjugate was prepared by coupling PEI to recombinant protein G (product of Sigma, catalog number P5170) through amide bonding, as follows.

5 mg of recombinant protein G was dissolved in 60 mg/ml of a PEI solution (pH 0.5) so as to give a final concentration of 0.5 mg/ml. 10 mg of EDC (product of PIERCE) was added to this protein G solution, and the mixture was stirred by means of a vortex mixer for 30 seconds, then allowed to stand overnight at 4° C., and deprived of the unreacted portion of PEI by dialysis against RO water (reverse osmosis membrane penetrating water) to give the title protein G-PEI conjugate.

Antibody Introduction into Cells Using Protein G-PEI Conjugate

A mixed solution containing the protein G-PEI conjugate prepared in the above manner and an antibody (introduction target protein and/or peptide) was added to an animal cell culture supernatant, and the intracellular introduction of the antibody with protein G-PEI as a carrier was studied. The antibody used for the introduction was rhodamine-rIgG. The introduction of the antibody into cells was evaluated by observation of the fluorescence of intracellular rhodamine.

A total amount of 50 µl of a mixed solution was prepared by mixing up a protein G-PEI solution, a rhodamine-rIgG solution and serum-free DMEM medium to a protein G-PEI concentration of 160 nM and a rhodamine-rIgG concentration of 587 nM, and the mixed solution was allowed to stand overnight at 4° C. Separately, a gelatin-coated glass was placed on the bottom of each well of a 24-well cell culture plate, about 20,000 Balb/c 3T3 (clone: A31-1-1) cells were sowed on the glass in each well, and the plate was allowed to stand overnight.

Figure 7A:
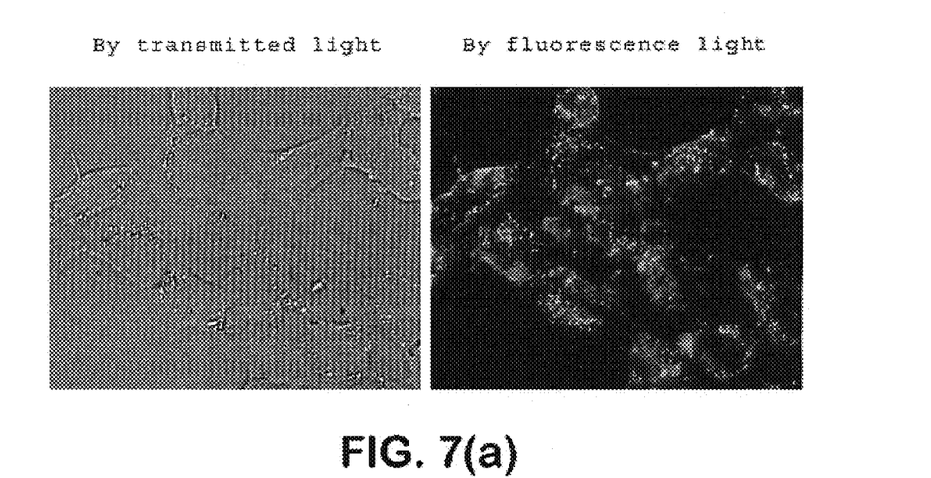
FIG. 7 shows observation views by fluorescent light and transmitted light, which show the incorporation of rhodamine-rIgG into cells. (a) are observation views of the cells which were cultured for 4 hours in a medium containing protein G-PEI and rhodamine-rIgG. (b) are observation views of the cells which were cultured for 4 hours in a medium containing protein G-PEI and rhodamine-rIgG, thereafter, the medium was replaced with complete medium, and cultivation was further continued for 24 hours.
Figure 7B:
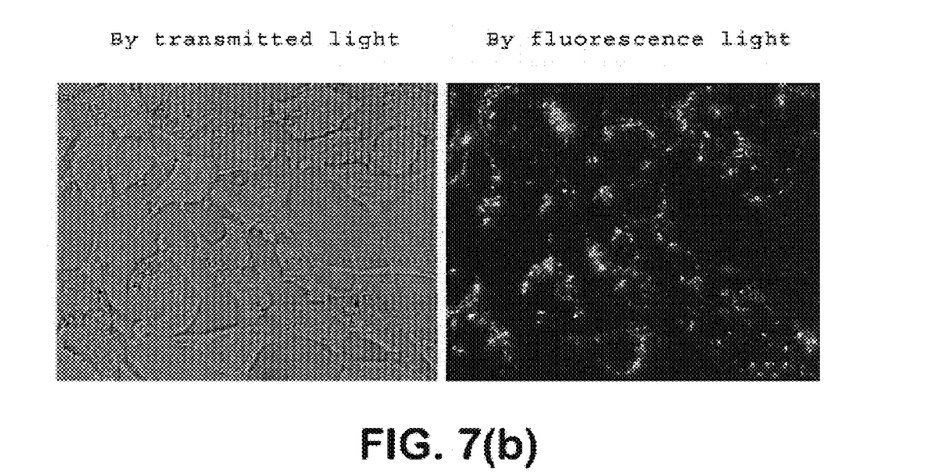

Then, 50 µl of the above mixed solution containing protein G-PEI and rhodamine-rIgG was 8-fold diluted with DMEM containing 10% FCS and, using this dilution as a cell culture medium, the above Balb/c 3T3 cells were cultured for 4 hours. The views obtained by observation of the culture in fluorescent light and transmitted light are shown in FIG. 7(a). After 4 hours of cultivation, the medium was replaced with complete medium (DMEM+10% FCS), and cultivation was further continued for 24 hours. The views of observation in fluorescent light and transmitted light are shown in FIG. 7(b).

EXAMPLE 6

Anti-IgG(H+L), Rabbit, Goat-Poly clonal antibody (product of Funakoshi, hereinafter referred to as "Antibody (H+L)") or Anti-IgG(Fc), Rabbit, Goat-Poly clonal antibody (product of Funakoshi, hereinafter referred to as "Antibody (Fc)") was used as the conjugate-forming protein and/or peptide. PEI (product of Wako Pure Chemical Industries, catalog number 161-17831; molecular weight 600, cation value 12) was used as the cationic group-containing polymer. FITC-Anti-IgG(H+L), Rat, Rabbit-Polyclonal antibody (human serum absorbed) (product of Funakoshi;, hereinafter referred to as "FITC-IgG") was used as the introduction target protein and/or peptide.

Preparation of Antibody (H+L)-PEI Conjugate and Antibody (Fc)-PEI

500 µl of a PEI solution with a concentration of 120 mg/ml (adjusted to pH 5.0 with hydrochloric acid) was added to 500 µl of an Antibody (H+L) solution with a concentration of 2.0 mg/ml, then 3 mg of EDC was added thereto, and the reaction was allowed to proceed at 4° C. for 16 hours. After completion of the reaction, the reaction mixture was sufficiently dialyzed against water at 4° C. and then incubated with a 0.5M hydroxylamine solution (pH 7.0) at 4° C. for half a day. The mixture was again sufficiently dialyzed against water and then against PBS for 1 day to give an Antibody (H+L)-PEI conjugate. With Antibody (Fc), the same procedure was followed to give an Antibody (Fc)-PEI conjugate.

Intracellular Introduction of FITC-IgG using Antibody (H+L)-PEI Conjugate or Antibody (Fc)-PEI Conjugate Since FITC-IgG is a rabbit-derived antibody, it is considered to bind to either of the Antibody (H+L)-PEI conjugate and Antibody (Fc)-PEI conjugate.

The following three samples were prepared:
(i) FITC-IgG (100 nM),
(ii) Mixed solution containing FITC-IgG (100 nM)+Antibody (H+L)-PEI conjugate (100 nM), and
(iii) Mixed solution containing FITC-IgG (100 nM)+Antibody (Fc)-PEI conjugate (100 nM).

The above three samples were allowed to stand on ice for 1 hour. The 3T3-SV-40 cell strain was cultured in DMEM+ 10% FBS. To the culture supernatant were respectively added the above samples and, after 4 hours of culture, the incorporation of FITC-IgG was observed in fluorescent light and transmitted light for each sample. The results are shown in FIG. 8.

Figure 8:
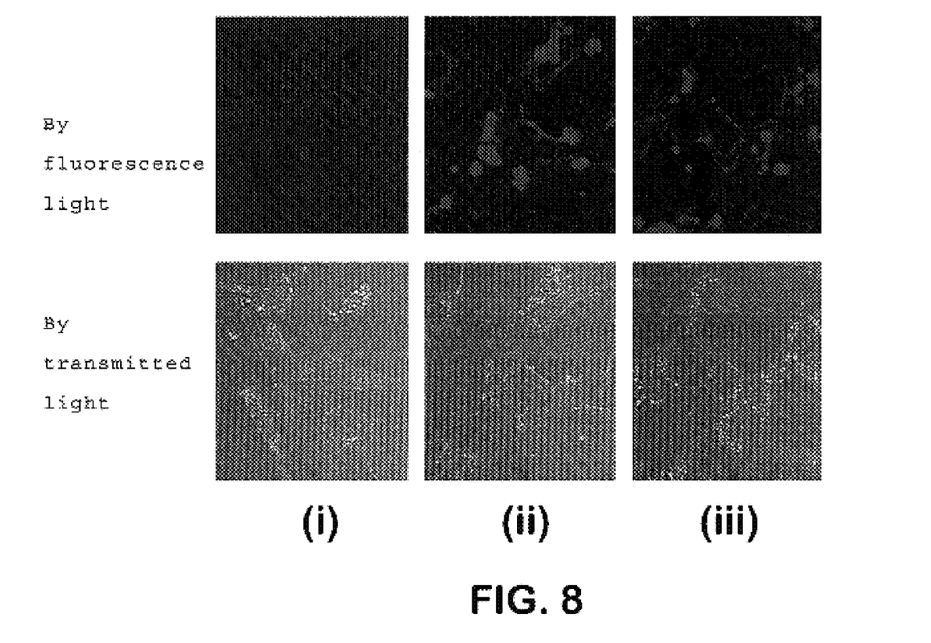
FIG. 8 shows observation views by fluorescent light and transmitted light, which show the incorporation of FITC-IgG into cells. (i) is an observation view using FITC-IgG, (ii) is using FITC-IgG+Antibody(H+L)-PEI conjugates solution, (iii) is using FITC-IgG+Antibody(Fc)-PEI conjugates solution.

As is evident from the observation results shown in FIG. 8, with the sample (i), almost no FITC-IgG was incorporated into cells because of the absence of any conjugate serving as a carrier. On the contrary, with either of the samples (ii) and (iii), FITC-IgG was efficiently incorporated into cells. Fluorescent observations were carried out with live cells, without fixation or like treatment.

INDUSTRIAL APPLICABILITY

The test kit for intracellular introduction and method of intracellular introduction according to the present invention, which respectively have the constitutions as described above, make it possible to introduce an arbitrary protein and/or peptide into cells in an efficient and expedient manner without impairing the function thereof. Thus, the test kit or intracellular introduction method of the present invention enables the introduction of a large number of cations through modification of a small number of amino acid side-chain, namely one to at most several side-chain, hence the structure and/or function of the protein and/or peptide is influenced only to a slight extent and it becomes possible to analyze the function of a protein and/or peptide whose function is unknown.

The present application claims priority under 35 U.S.C. §119 to Japanese Patent Application No. 2002-287280, filed Sep. 30, 2002, entitled "METHOD OF INTRODUCING A PROTEIN INTO CELLS".

The contents of these applications are incorporated herein by reference in their entirety.

The invention claimed is:

1. A method of introducing a protein and/or peptide into cells
   which comprises using a conjugate generated by coupling or binding of a cationic group-containing polymer to a protein and/or peptide as a carrier for the introduction target protein and/or peptide,
   wherein the cationic group-containing polymer has a number average molecular weight of not more than 3000.

2. The method of intracellular peptide and/or peptide introduction according to claim 1,
   wherein said conjugate-forming protein and/or peptide comprises at least one protein and/or peptide selected from the group consisting of avidins, protein A and/or protein G, and antibodies.

* * * * *